United States Patent
Umar

(10) Patent No.: US 10,159,508 B2
(45) Date of Patent: Dec. 25, 2018

(54) FOLLICLE PUNCH FOR USE WITH CURLED FOLLICLES

(71) Applicant: Sanusi Umar, Redondo Beach, CA (US)

(72) Inventor: Sanusi Umar, Redondo Beach, CA (US)

( * ) Notice: Subject to any disclaimer, the term of this patent is extended or adjusted under 35 U.S.C. 154(b) by 68 days.

(21) Appl. No.: 14/388,044

(22) PCT Filed: May 13, 2014

(86) PCT No.: PCT/US2014/037832
§ 371 (c)(1),
(2) Date: Sep. 25, 2014

(87) PCT Pub. No.: WO2015/005970
PCT Pub. Date: Jan. 15, 2015

(65) Prior Publication Data
US 2016/0249948 A1    Sep. 1, 2016

Related U.S. Application Data

(63) Continuation-in-part of application No. PCT/US2013/071991, filed on Nov. 26, 2013.
(Continued)

(51) Int. Cl.
*A61B 17/50* (2006.01)
*A61B 17/3205* (2006.01)
(Continued)

(52) U.S. Cl.
CPC .......... *A61B 17/32053* (2013.01); *A61F 2/10* (2013.01); *A61B 2017/00752* (2013.01); *A61B 2017/320064* (2013.01)

(58) Field of Classification Search
CPC ...... A61B 17/32053; A61B 17/320068; A61B 17/3468; A61B 2017/00752;
(Continued)

(56) References Cited

U.S. PATENT DOCUMENTS

2007/0156164 A1*  7/2007  Cole ................ A61B 17/32053
                                                        606/187
2007/0293884 A9   12/2007  Cole et al.
(Continued)

OTHER PUBLICATIONS

International Search Report and Written Opinion; PCT/US14/37832 (of which this is a "371" application).

*Primary Examiner* — Elizabeth Houston
*Assistant Examiner* — Mohamed Gabr
(74) *Attorney, Agent, or Firm* — Law Office of Michael O'Brien

(57) ABSTRACT

A punch that is particularly useful for removing curled hair follicles from a donor site comprises a generally tubular body disposed about a generally longitudinal axis between distal and proximal ends, and having a distal cutting end region terminating distally in an opposing pair of distally-extending, generally prong-like members having an anterior notch and a posterior notch therebetween. In one variation, the prong-like members each have a curved anterior cutting edge and a curved posterior edge meeting at a cutting tip. In the preferred embodiment, the posterior notch extends proximally further than the anterior notch and has a generally "V"-shaped distal segment which carries cutting edges together with a generally "U"-shaped proximal segment extending proximally from the distal segment.

17 Claims, 9 Drawing Sheets

Related U.S. Application Data

(60) Provisional application No. 61/985,347, filed on Apr. 28, 2014, provisional application No. 61/729,733, filed on Nov. 26, 2012, provisional application No. 61/874,664, filed on Sep. 6, 2013.

(51) Int. Cl.
 *A61F 2/10* (2006.01)
 *A61B 17/32* (2006.01)
 *A61B 17/00* (2006.01)

(58) Field of Classification Search
 CPC ....... A61B 2017/320096; A61B 2017/320064; A61F 2/10; A45D 26/00
 See application file for complete search history.

(56) References Cited

U.S. PATENT DOCUMENTS

2008/0234698 A1\* 9/2008 Oostman ............ A61B 10/0266 606/133
2008/0234699 A1 9/2008 Oostman, Jr. et al.

\* cited by examiner

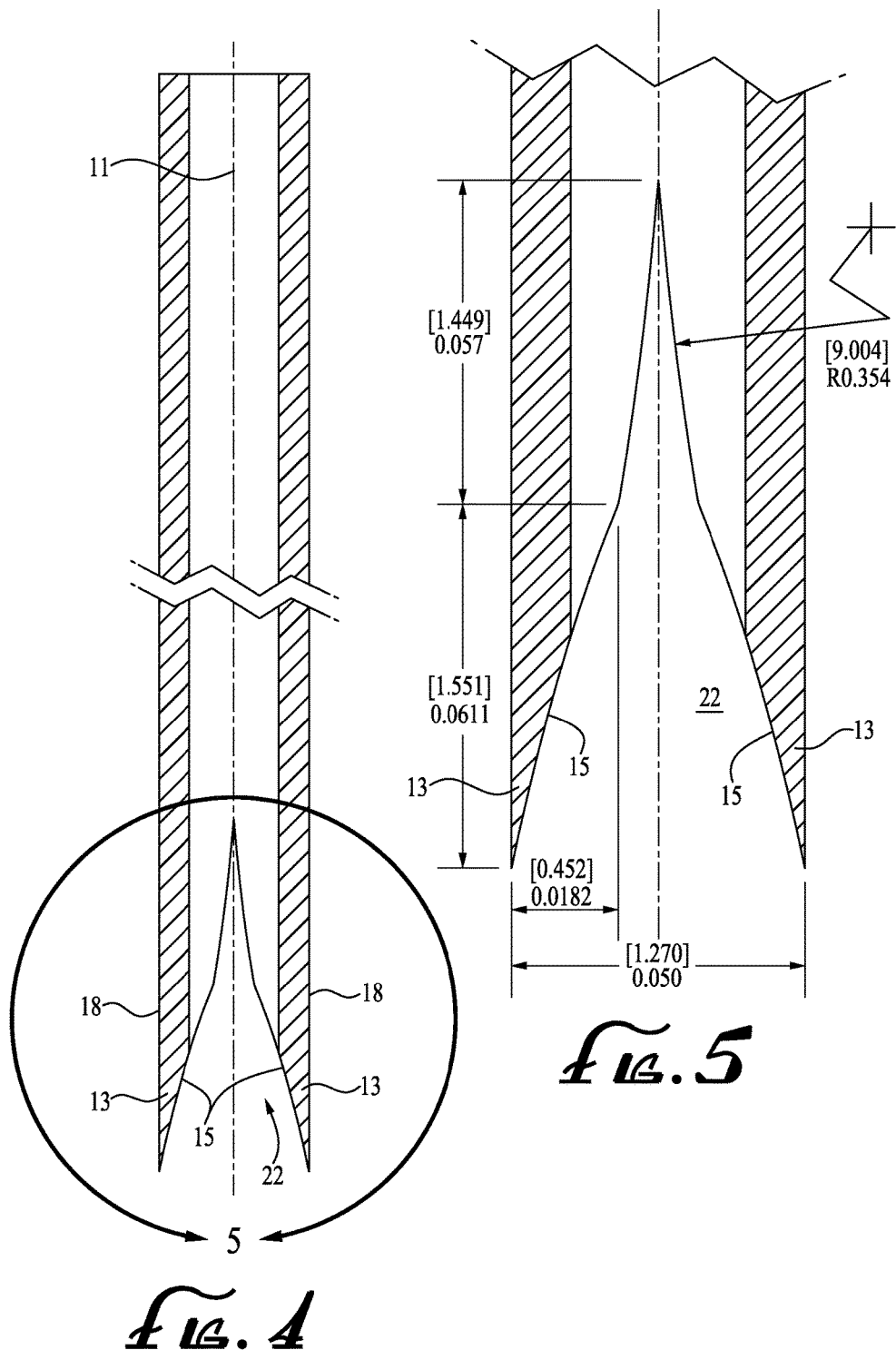

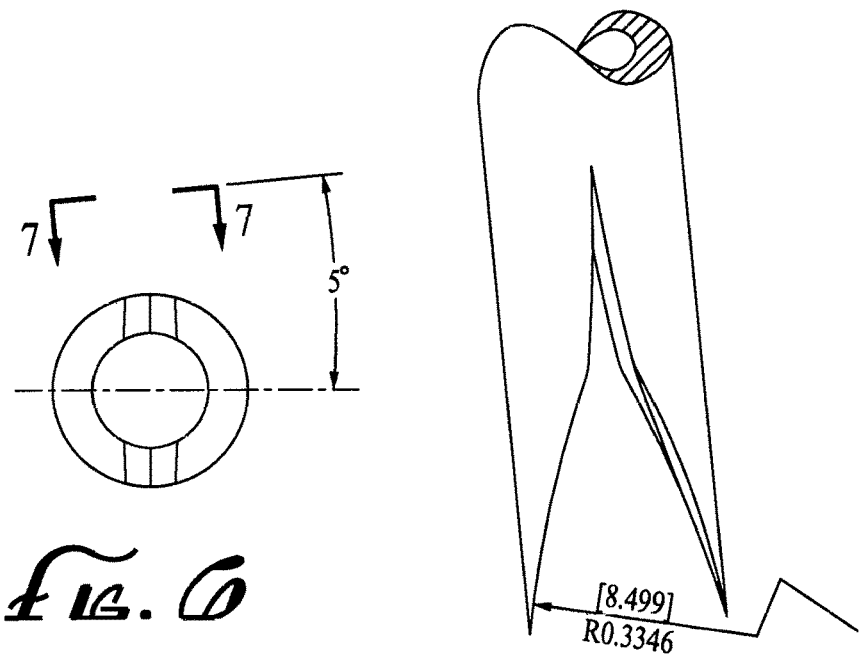
FIG. 6
FIG. 7
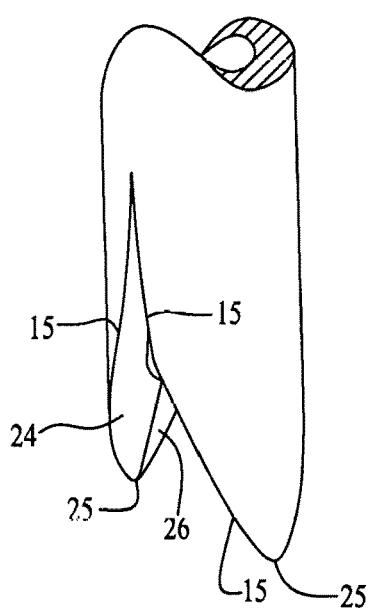
FIG. 8
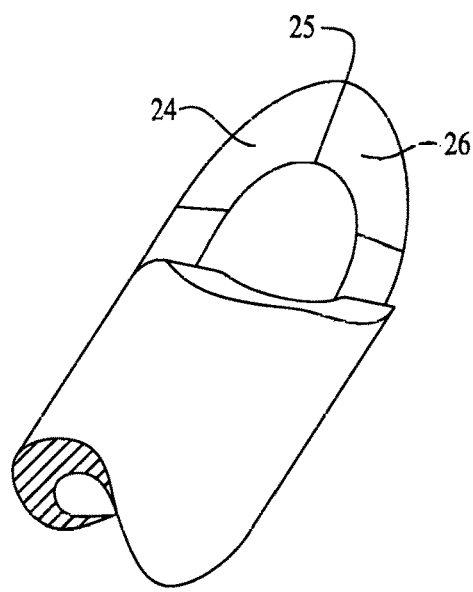
FIG. 9

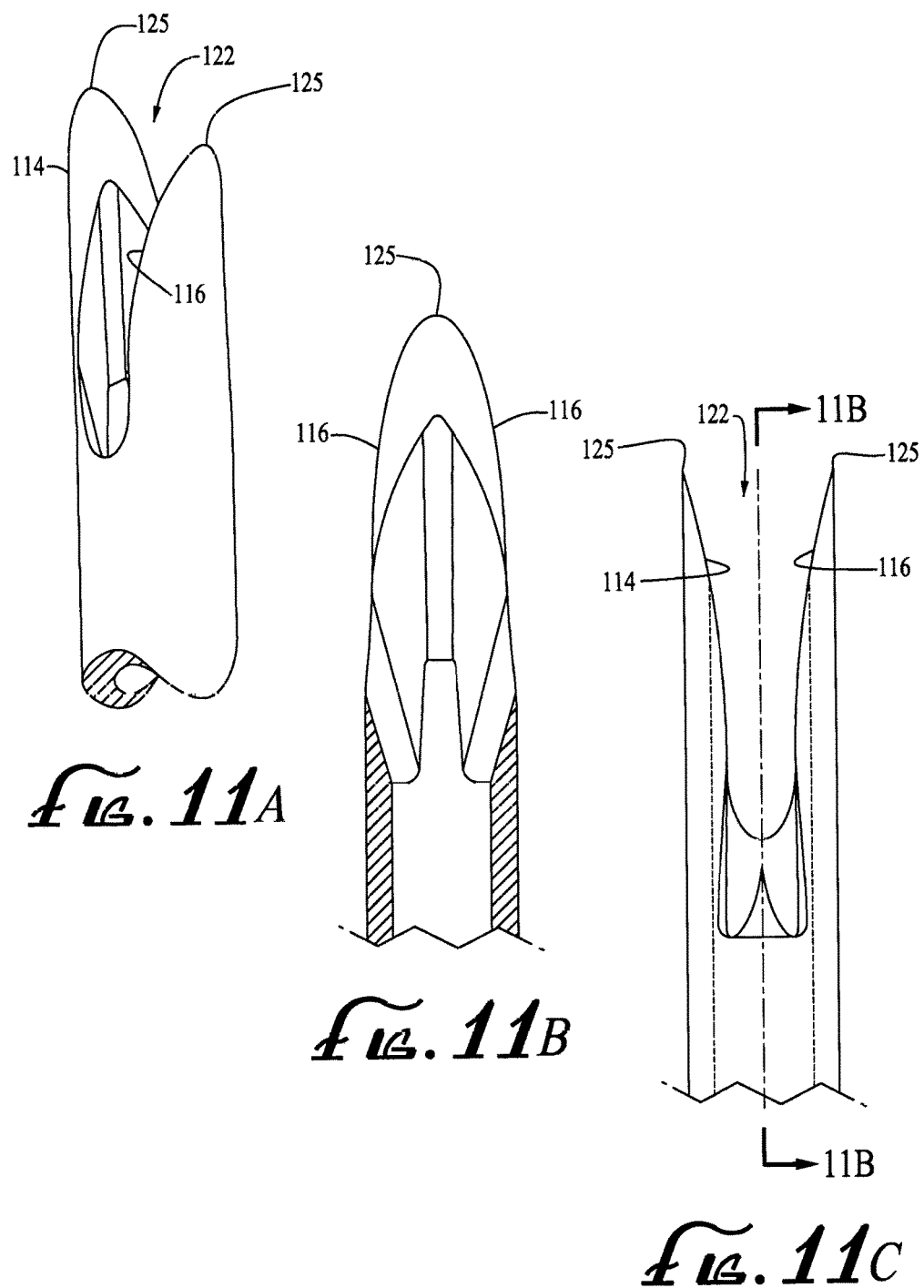

US 10,159,508 B2

FOLLICLE PUNCH FOR USE WITH CURLED FOLLICLES

FIELD OF THE INVENTION

This invention relates to surgical instruments and, more particularly, to a punch for extracting hair follicles from the skin.

BACKGROUND OF THE INVENTION

Hair transplantation is a surgical technique that involves moving skin containing hair follicles from one part of the body (the donor site) to bald or balding parts (the recipient site).

Hair naturally grows in follicles that contain groupings of 1 to 4 hairs, and transplant techniques typically move the 1-4 hair "follicular units" from the donor site to the recipient site. Hair follicles grow at an angle to the skin, pointing from anterior to posterior.

The follicles of hair are typically removed from the donor site using punches of between 0.7 mm and 1.25 mm in diameter. The punches are tubular bodies having a skin-contacting cutting edge, and are typically mounted in a tool that causes the punch to rotate as the punch is brought into contact with the donor site. Hair follicles are very easily damage during the removal process, and damaged follicles are unlikely to be successfully transplanted.

Curled follicles are extremely susceptible to damage by follicle punches and are therefore particularly difficult to extract for successful transplantation. Such follicles are curled beneath the skin and are easily cut and/or damaged by the advancing cutting edge of conventional punches as the punch penetrates the donor site's tissue.

SUMMARY OF THE INVENTION

A punch that is particularly useful for removing curled hair follicles from a donor site comprises a generally tubular body disposed about a generally longitudinal axis and having a distal cutting end region terminating distally in a plurality of distally-extending circumferentially disposed, generally prong-like members carrying distally diverging cutting edges and separated by follicle-accommodating slits or slots. As used herein, the terms "slit" and "slot" are both used because the primary difference, as used herein, is subjective when working with dimensions of the small magnitudes discussed herein.

In practice, the punch is oriented during the extraction process at the donor site so that the curled hair root passes into, and is spared from the advancing cutting edge by, a slit as the punch is inserted into and penetrates the tissue. The punch may then rotated slightly so that the cutting edges cut most of the tissue surrounding the follicle without making damaging contact with the follicle. It may be noted that a rotary motion may not be necessary and, if rotation is desired, it may be in one direction or be in the form of an oscillatory rotary movement, depending on characteristics of the donor site and targeted follicle.

The foregoing insertion process may be performed manually or under machine or computer control, and with or without the aid of an ultrasonic transducer coupled to punch to impart a vibratory cutting force against the tissue. In addition, a mechanism for automatically rotating the punch may be employed, and may accordingly be coupled to the ultrasonic transducer if one is used.

These and further details of the invention will be apparent to those of ordinary skill in the art from reading a description of the currently preferred embodiment of the invention described below, of which the drawing forms a part.

DESCRIPTION OF THE DRAWING

FIG. 4 is a longitudinal section view of the punch of FIG. 1, taken along line 4-4 in FIG. 2;

FIG. 5 is an enlarged fragmentary view of the portion of the punch illustrated within the line 5 of FIG. 4;

FIG. 6 is a bottom plan view of the punch of FIG. 2;

FIG. 7 is a fragmentary view in perspective of the cutting end region of the punch oriented per line 7-7 in FIG. 6 illustrated in FIG. 1;

FIG. 8 is an oblique fragmentary elevation view of the cutting end region of the punch of FIG. 1;

FIG. 9 is an oblique bottom view of the cutting end region of the punch of FIG. 1;

FIG. 11A is a right front oblique view, in schematic, of an alternative embodiment of a punch that is constructed in accordance with the invention for removing hair follicles;

FIG. 11B is a longitudinal sectional view of the punch of FIG. 11A, taken along line 11B-11B in FIG. 11C;

FIG. 11C is a front elevation view, in schematic, of the punch of FIG. 11A,

DETAILED DESCRIPTION

Figures 1, 2, 3:
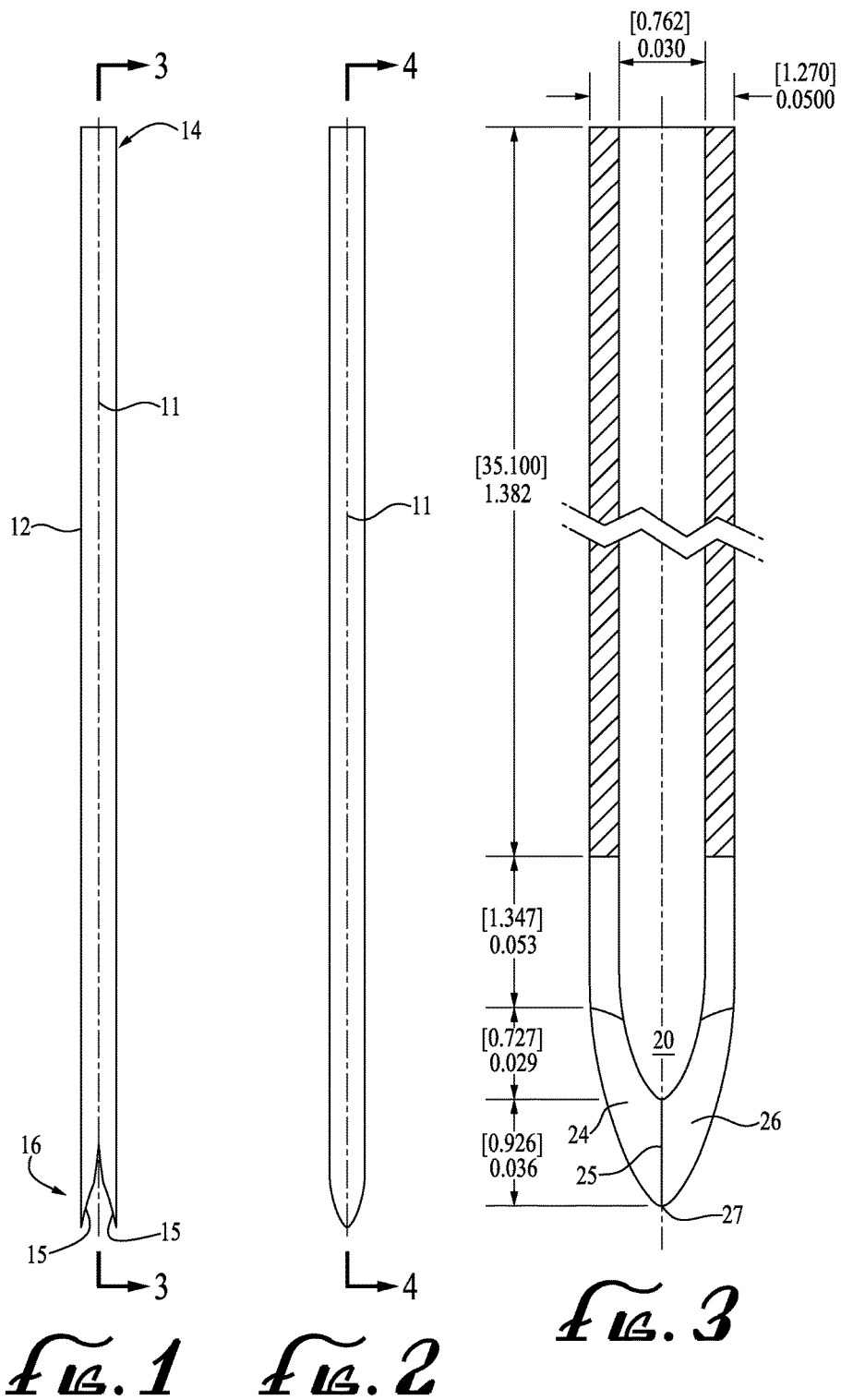
FIG. 1 is a front elevation view of a punch for removing hair follicles that is constructed in accordance with the invention.
FIG. 2 is a side elevation view of a punch of FIG. 1.
FIG. 3 is a longitudinal section view of the punch of FIG. 1, taken along line 3-3 in FIG. 1.

Referring to FIGS. 1-9, a punch for extracting curled follicles is illustrated as comprising a generally tubular body 12 extending from a proximal end 14 to a skin-contacting distal end 16 about a generally central longitudinal axis 11. The currently preferred dimensions of the punch are displayed in the Figures in both inches (unbracketed) and millimeters (bracketed), said currently preferred dimensions being part of this Detailed Description.

The punch's generally tubular body 12 has a distal cutting end region terminating distally in a plurality of distally-extending circumferentially disposed, generally prong-like members 13 carrying distally diverging cutting edges 15 separated by follicle-accommodating slits 22. The currently preferred number of members 13 is two because a pair of such members currently appears to provide the appropriate amount of cutting around the follicle together with sufficient slit width to safely accommodate entry and protection of the follicle during the extraction process.

As illustrated in the Figures, each of the preferred prong-like members 13 has a generally convex outer surface 18 and a generally concave inner surface 20 substantially the same as that of the tubular body. As also illustrated in the Figures, each of the prong-like members also has a beveled cutting surface 24, 26 terminating at a cutting edge 15, with the bevel preferably being on the inside of the punch so that it terminates at a cutting edge on the punch's outer diameter. However, the formation of bevels on the outer surface of the punch is also possible, although not preferred, and is within the scope of the invention. It may be noted that it is currently believed that the cutting edge portion illustrated in FIG. 3 as 1.653 mm in length may be as long as approximately 4 mm or so, and that the follicle-accommodating slit 22 should preferably be approximately 2 mm-4 mm longer than the cutting edge portion.

The bevels 24, 26 are preferably created by grinding cutting edges outwardly from the interiors of the members 13 to produce sharp cutting edges. However, the bevels can also be formed by laser cutting, waterjet or abrasivejet cutting, chemical molding, and/or other manufacturing processes without departing from the scope of the invention.

The bevels 24, 26 preferably interface at an apex 25 of the prong-like member to provide a sharp, point-like, leading tip 27 which makes the initial penetration into the tissue that surrounds the targeted follicle, while the widening, generally semi-elliptical profiles of the prong-like members 13 cut more of the surrounding tissue as the punch is urged distally into the site. The leading tip can alternatively be a sharp rounded tip without departing from the scope of the invention.

The distal end region of the punch may be further provided with generally circumferentially-extending notch having a generally concave shape that generally circumscribes the punch's outer surface. The notch preferably extends 1-2 mm proximally from a location closely adjacent the tip of the punch. The generally concave shape serves two purposes. First, its preferred size and shape results in a wound with everted edges; as the punch enters the tissue surrounding the targeted follicle, the tissue outward of the cut expands against the concavity as it is passed by the cutting edge. When the punch is subsequently withdrawn, the tissue resumes its consequently everted shape. Second, the generally concave shape and preferred sharpening from the inside of the punch results in a cutting force that is outwardly directed away from the follicle and tissue to be extracted, decreasing the risk of damage to the follicle.

Alternatively, the punch can be provided with a flared distal end having a diameter that has a diverging inner diameter and diverging outer diameter along the last 1 mm or so, with the flared end region resulting in a preferred gap of approximately 1.25 mm between opposing tips. Gaps of great or lesser spacing may be utilized as well, depending on the subject's hair and follicle dimensions without departing from the scope of the invention.

In one preferred configuration, the shape and dimensions of the slit 22 are, as best illustrated in FIGS. 4 and 5, a general inverted "V" profile having a relatively distal segment 22b and a relatively proximal segment 22a that is more steeply tapered than the distal segment 22b. The more steeply tapered interior of the relatively proximal segment provides a slit length and width that accommodates the follicle as the punch penetrates the surrounding tissue, in order to spare the follicle from being cut; the less tapered distal segment of the slit results in adequate spacing of the cutting edges of adjacent prong-like members 13 from the follicle's root structure so that the cutting yields a viable implant. Although the same taper could be used for both segments, it is preferable not to do so since a generally uniformly steep taper (such as that of the preferred distal segment) would add unnecessary length to the punch to achieve the needed spacing between the prongs, while a generally uniformly shallow taper (such as that of the preferred distal segment) would fail to provide the slit length needed.

The cutting edge of the punch, which preferably extends from its leading tip to the beginning of the steeply tapered portion of the slit (i.e., the interface of the proximal and distal slit segments), may be smooth or include one or more serrations. If serrations are included, it is currently preferable that there be one or two serrations, with rounded edges, although the use of sharply angled edges would not depart from the scope of the invention.

Figure 10:
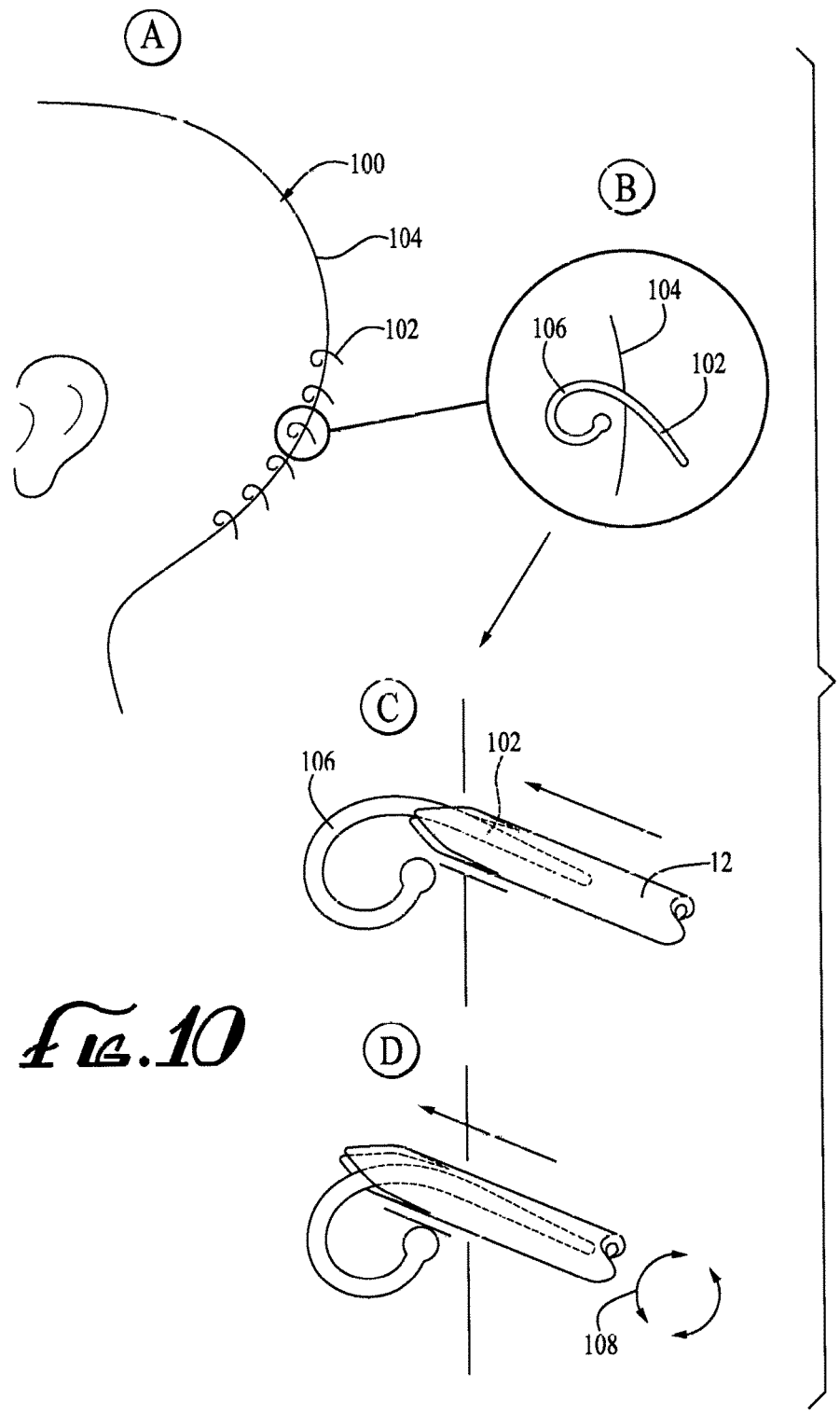
FIG. 10 is a schematic illustration of the preferred methodology for extracting a curled follicle in accordance with the invention.

FIG. 10 schematically illustrates (at "A") a subject's head 100 having a plurality of hairs 102 protruding from the skin 104. A hair 102 and its curled, subcutaneously-located follicle 106 is schematically illustrated in magnified form at "B".

As next schematically illustrated with greater magnification at "C", the punch is inserted into the skin at the donor site in such a way that the hair enters the punch's interior while the follicle 106 passes uncut through the slit 22. As further illustrated at "D", the punch is advanced past the follicle, which remains undamaged by the cutting edges of the punch by passing through the slit. Once the punch has penetrated sufficiently, it can be partially rotated back and forth if desired, as schematically illustrated by the arrows, resulting in an arcuate cut in the tissue substantially circumscribing the curled follicle, while the follicle itself is spared by its clearance within the slit and isolation from the cutting edges. The intact hair follicle is then removed from the donor site for subsequent transfer to the recipient site.

To penetrate the skin, the punch could be manually pressed proximally by hand. Currently, it is believed that the use of an ultrasonic transducer to apply rapid, incremental, proximally-directed cutting force pulses to the tissue via the punch offers a more precisely controllable methodology for penetrating the tissue while the punch is positioned at the donor site and oriented so as to accommodate the follicle within the slit.

Turning to FIGS. 11A-C, another variation a follicle punch constructed in accordance with the invention is illustrated. It should be noted that the interior surfaces of the punch are smooth; the apparent facets illustrated in FIGS. 11A and 11B are computer-generated "tangent" lines connoting a change in surface direction only.

The punch illustrated in FIGS. 11A-C comprises a pair of distally-extending circumferentially disposed, generally prong-like members 113 carrying distally diverging cutting edges 114, 116 and separated by a generally U-shaped follicle-accommodating slit 122. The cutting edge of each prong-like member is again preferably formed from the inside of the punch by grinding cutting edges outwardly from the interior region of the members. However, as noted earlier, the cutting edges can also be formed by laser cutting, waterjet or abrasivejet cutting, chemical molding, and/or other manufacturing processed without departing from the scope of the invention. The leading tips 125 of the punch illustrated in FIGS. 11A-C are sharp rounded tips that make the initial penetration into the skin and tissue surrounding the targeted follicle.

To minimize the risk of the follicle being cut during the extraction process, the formation of the cutting edges may be limited to the first 0.060 inches (1.52 mm) or so from the distal tip 125 of the punch, so that the cutting edges pass the follicle during insertion of the punch at the donor site and any subsequent contact between the punch and follicle is not with a cutting edge. The cutting edge may however extend the entire length, or a different length, of the slits.

The gap between the prong-like members of the punch illustrated in FIGS. 11A-C is preferably 0.02-0.03 inches (0.51-0.76 mm) wide. It preferably extends proximally from the distal tip of the punch for about 0.12 to 0.16 inches (3.05-4.06 mm).

Figures 12A, 12B, 12C:
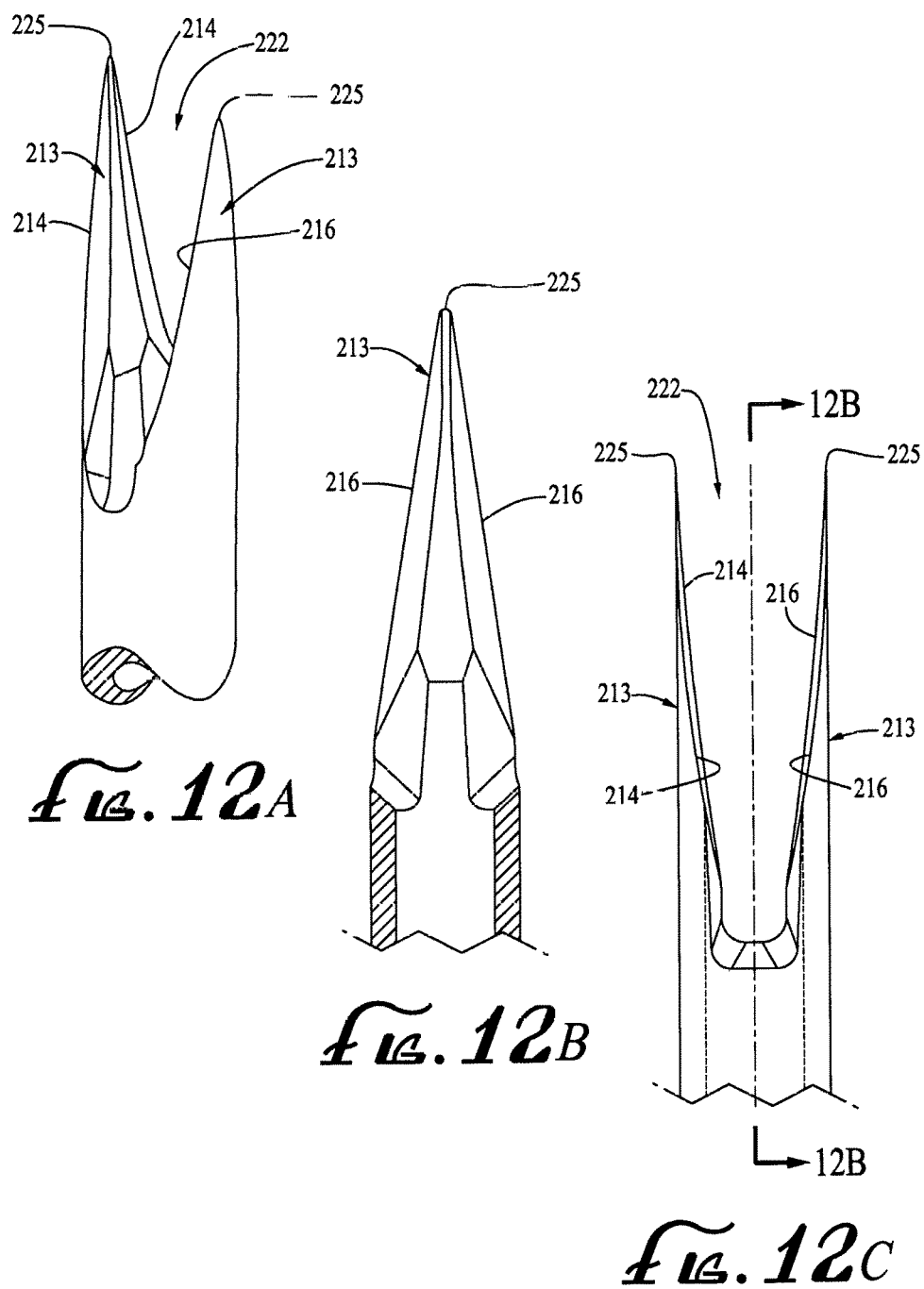
FIG. 12A is a right front oblique view, in schematic, of a second alternative embodiment of a punch that is constructed in accordance with the invention for removing hair follicles.
FIG. 12B is a longitudinal sectional view of the punch of FIG. 12A, taken along line 12B-12B in FIG. 12C.
FIG. 12C is a front elevation view, in schematic, of the punch of FIG. 12A.

Turning to FIG. 12A-C, another variation of the punch is illustrated, wherein the punch comprises a pair of distally-extending circumferentially disposed generally prong-like members 213 that carry distally-diverging cutting edges 214, 216 separated by a generally U-shaped follicle-accommodating slit. The leading tips 225 of the members 213 are sharp pointed tips. Each cutting edge 214, 216 is preferably formed from the inside of the punch by grinding cutting edges outwardly from the interior region of the prong-like members. However, as noted earlier, the cutting edges can also be formed by laser cutting, waterjet or abrasivejet cutting, chemical molding, and/or other manufacturing processed without departing from the scope of the invention. To minimize the risk of the follicle being cut during the extraction process, the formation of the cutting edges may be limited to the first 0.060 inches (1.52 mm) or so from the distal tip of the punch, so that the cutting edges pass the follicle during insertion of the punch at the donor site and any subsequent contact between the punch and follicle is not with a cutting edge. The cutting edge may however extend the entire length, or a different length, of the gap.

The gap between the prong-like members of the punch illustrated in FIGS. 12A-C is preferably 0.03 inches (0.076 mm) wide, and preferably extends proximally from the distal tip of the punch for about 0.16 inches (4.06 mm).

As with FIGS. 11A-B, it should be noted that the interior surfaces of the punch illustrated in FIGS. 12A-B are smooth, and that the apparent facets are computer-generated "tangent" lines connoting a change in surface direction only.

Figures 13A, 13B, 13C:
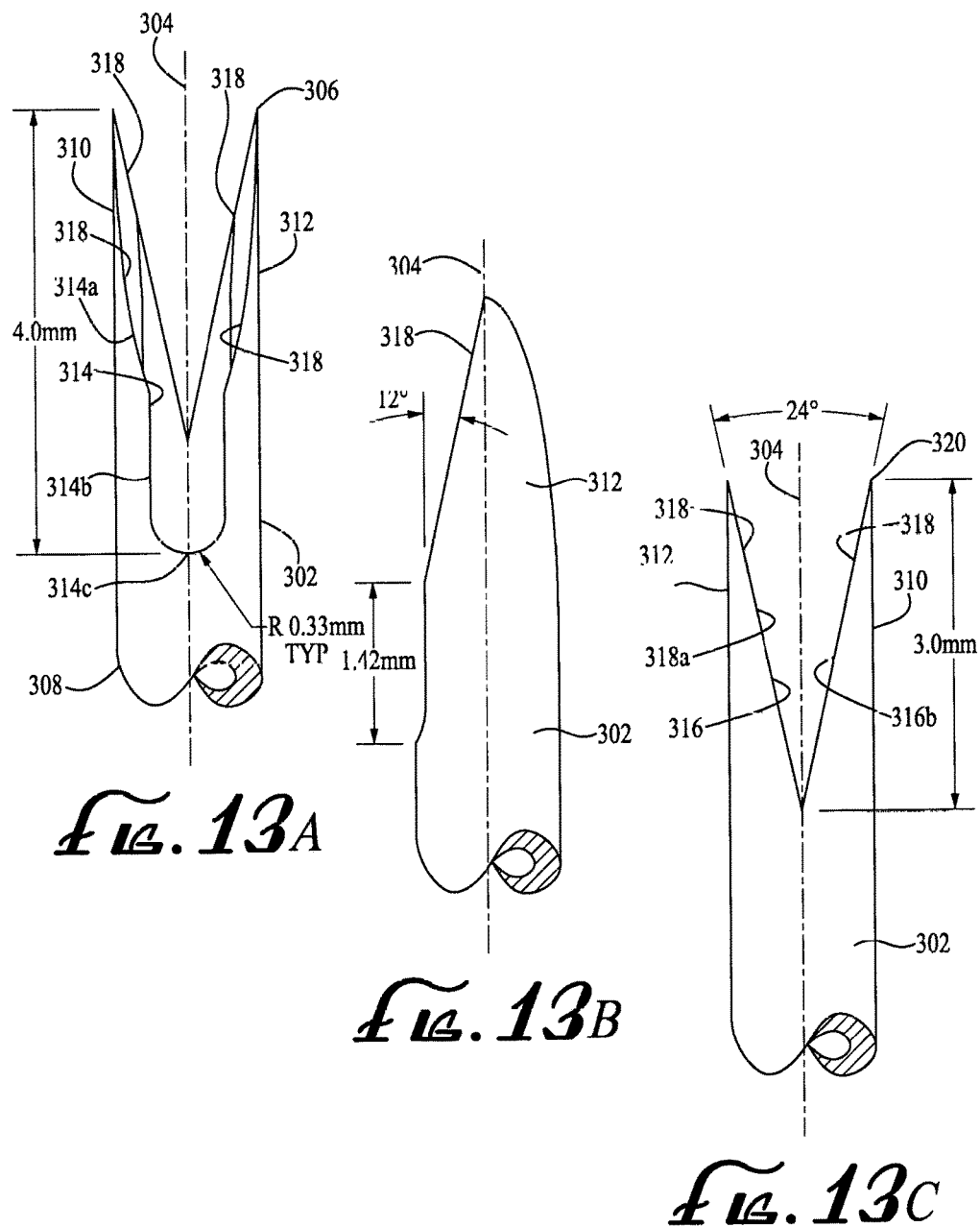
FIG. 13A is a rear elevation view, in schematic, of the currently preferred embodiment of the distal end region of a punch constructed in accordance with the invention for removing hair follicles from patients with straight or wavy hair.
FIG. 13B is a left side elevation view, in schematic, of the distal end region illustrated in FIG. 13A.
FIG. 13C is a front elevation view, in schematic, of the distal end region illustrated in FIG. 13A.

FIG. 13A is a rear elevation view, in schematic, of the distal end region of the currently preferred punch for removing hair follicles from patients with straight or wavy hair, while FIG. 13B is a left side elevation view, in schematic, of the distal end region illustrated in FIG. 13A and FIG. 13C is a front elevation view, in schematic, of the distal end region illustrated in FIG. 13A. The distal end region illustrated in FIGS. 13A-C, comprises a generally tubular body 302 disposed about a generally longitudinal axis 304 between distal and proximal ends 306, 308, and having a distal cutting end region terminating distally in an opposing pair of distally-extending, generally prong-like members 310, 312 having posterior and anterior notches 314, 316 therebetween. The tubular body is preferably formed from stainless steel having a thickness in the range of 15-22 gauge (i.e., 0.0673-0.0299 inches; 1.709-0.759 mm). For exemplary purposes, an 18 gauge thickness (0.0478 inches; 1.214 mm) will be used herein.

Each of the prong-like members carries cutting edges 318 preferably formed by a respective beveled surface within the generally tubular body that terminates at the cutting edge so that the cutting edge is formed at the outer surface (i.e., the outer diameter) of the generally tubular body. Preferably, the cutting edge extends completely around the prong-like member, and may be serrated or (preferably) non-serrated. The preferred bevel is created by sharpening the generally tubular body from the inside at a 15° angle.

As illustrated in FIGS. 13A and 13C, the currently preferred posterior notch 314 extends further in the proximal direction than the currently preferred anterior notch 316, and is shaped differently. Turning first to the preferred anterior notch best shown in FIG. 13C, the notch 316 is generally V-shaped, comprising two proximally extending legs 316a, 316b that carry respective cutting edges formed by respective beveled surfaces. The apex of the "V" is approximately 0.118 inches (3 mm) proximally from the tip 320 of the prong-like member. The legs 316a, b of the notch each extend at a preferred angle of approximately 12° with respect to the longitudinal axis 304, resulting in angle of convergence of approximately 24°.

The currently preferred posterior notch 314, best illustrated in FIG. 13A, comprises a generally "V"-shaped distal segment 314a, and a generally "U"-shaped proximal segment 314b that extends proximally from the distal segment. The U-shaped segment includes two proximally extending legs connected by a generally laterally extending base 314c at the proximal end of the notch. Preferably, and for reasons described later, the proximally-extending legs of the U-shaped segment carry respective sharpened cutting edges formed by respective beveled surfaces, while the base 314c lacks a sharpened cutting.

The currently preferred generally V-shaped distal segment 314a of the posterior notch is approximately 0.097 inches (2.46 mm) proximally of the tip 306. The base 314c lies approximately 0.157 inches (4 mm) proximally of the tip 306; i.e. 0.039 inches (1 mm) proximally further from the tip than the apex of anterior notch's apex. In practice, a difference in the range of 0-0.12 inches (0-3 mm) is acceptable for reasons described later. Preferably, the angle of convergence of the legs of the posterior notch's V-shaped segment is the same as that of the anterior notch's legs 316a, b.

Figures 14A, 14B, 14C:
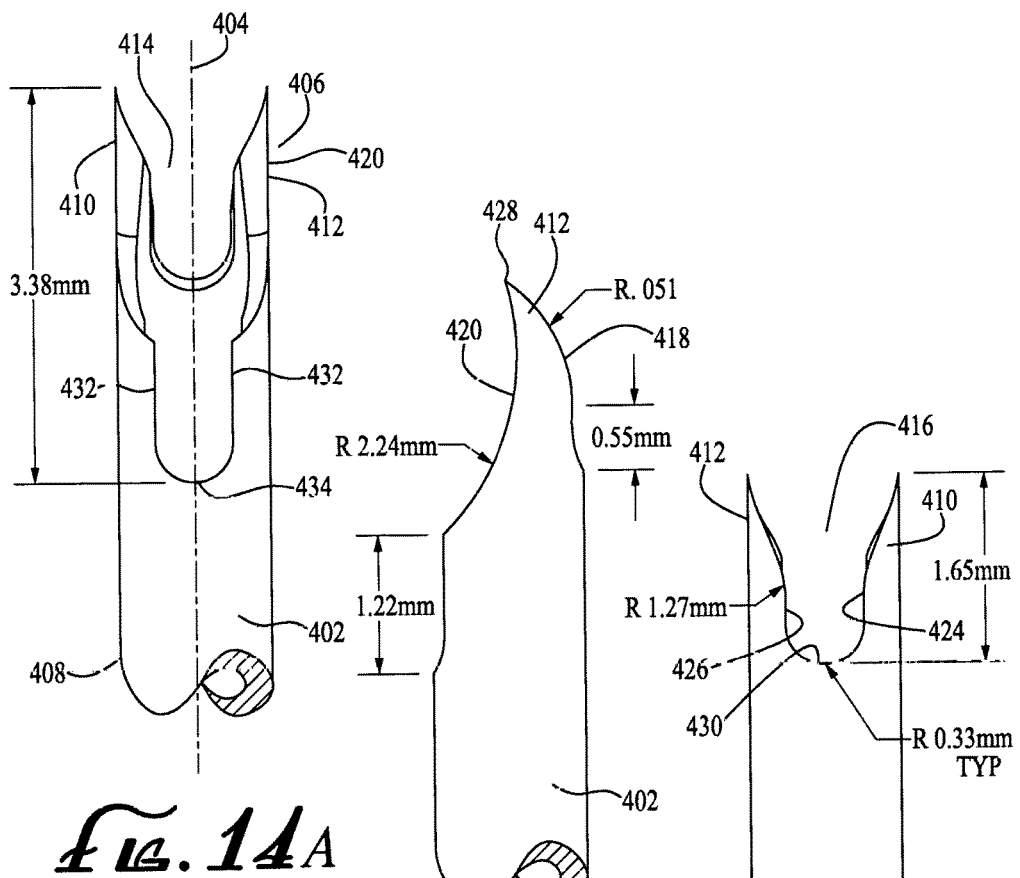
FIG. 14A is a rear elevation view, in schematic, of the currently preferred embodiment of the distal end region of a punch constructed in accordance with the invention for removing hair follicles from patients with kinky Afro-textured hair.
FIG. 14B is a left side elevation view, in schematic, of the distal end region illustrated in FIG. 14A.
FIG. 14C is a front elevation view, in schematic, of the distal end region illustrated in FIG. 14A.

FIG. 14A is a rear elevation view, in schematic, of the distal end region of the currently preferred punch constructed in accordance with the invention for removing hair follicles from patients with kinky Afro-textured hair, while FIG. 14B is a left side elevation view, in schematic, of the preferred distal end region illustrated in FIG. 14A and FIG. 14C is a front elevation view, in schematic, of the preferred distal end region illustrated in FIG. 14A.

As illustrated in FIGS. 14A-C, the preferred punch's distal end region comprises a generally tubular body 402 disposed about a generally longitudinal axis 404 between distal and proximal ends 406, 408, and has a distal cutting end region terminating distally in an opposing pair of distally-extending, generally prong-like members 410, 412 having posterior and anterior notches 414, 416 therebetween. The prong-like members each have a convex curved anterior cutting edge 418 and a concave curved posterior cutting edge 420 meeting at a cutting tip 428. As illustrated in FIG. 14B, the cutting tip 418 of each prong-like member is oriented at an angle relative to the longitudinal axis of the generally tubular body towards the curved posterior cutting edge 420. The prong-like members are preferably aligned with each other in the longitudinal and lateral directions (i.e., in the directions transverse to the longitudinal axis) as illustrated in FIGS. 14A-C, and have essentially the same shape as each other. By way of example, one preferred tubular body formed from 18 gauge stainless steel (a thickness of 0.0478 inches (1.214 mm)) terminates in prong-like members having a curved anterior edge characterized by a 0.051 inch radius of curvature and a posterior cutting edge characterized by a 0.088 inch (2.24 mm) radius of curvature.

As with the punch of FIGS. 13A-C, the punch of FIGS. 14A-C preferably has a posterior notch 414 extending further proximately than the anterior notch 416 by a length in the range of 0 mm to 3 mm, inclusive. Turning first to the preferred anterior notch best shown in FIG. 14C, the notch 416 has a proximal segment that is generally U-shaped, comprising two proximally extending legs 424, 426 that preferably carry sharpened cutting edges. The legs 424, 426 are linked at their proximal end by a curved lateral segment 430 having, by way of example, a radius of curvature of 0.013 inches (0.33 mm) approximately 0.065 inches (1.65 mm) proximal of the cutting tip. The anterior notch further comprises a distal generally "V"-shaped segment that interfaces with the proximal segment approximately 0.043 inches (1.09 mm) proximally from the tips 428.

The currently preferred posterior notch 414, best illustrated in FIG. 14A, comprises a generally "U"-shaped posterior notch segment formed by two proximally extending legs 432 connected by a curved generally laterally extending base 434 at the proximal end of the notch. Preferably, and for reasons described later, the proximally-extending legs of the U-shaped segment carry respective cutting edges formed by respective beveled surfaces, while the laterally-extending base 434 lacks a sharpened cutting edge.

The legs 432 of the illustrated posterior notch interface with the prong-like members approximately 0.085 inches (2.16 mm) proximally from the tips 428. The laterally-extending base 434 is approximately 0.133 inches (3.38 mm) proximally from the tips. Accordingly, the posterior notch 414 extends approximately 0.083 inches (2.1 mm) further from the tips than the anterior notch 416.

Figure 15:
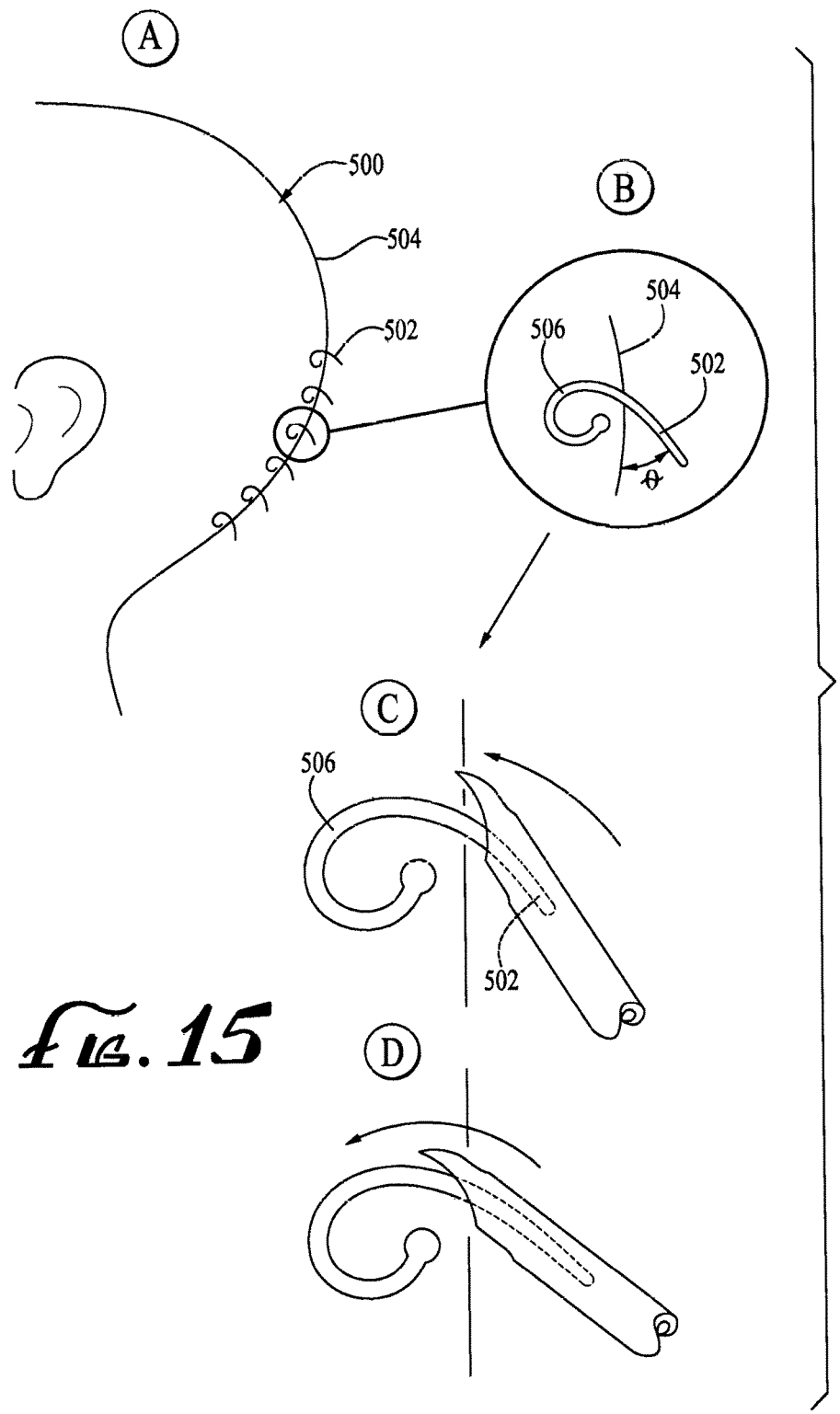
FIG. 15 is a schematic illustration of the preferred methodology for extracting a curled follicle using the punch of FIGS. 14a-c in accordance with the invention.

FIG. 15 schematically illustrates (at "A") a subject's head 500 having a plurality of hairs 502 protruding from the skin 504. A hair 502 and its curled, subcutaneously-located follicle 506 is schematically illustrated in magnified form at "B". The hair follicle grow at an angle $\Theta$ to the skin, pointing from anterior to posterior.

As next schematically illustrated with greater magnification at "C", the preferred punch of FIGS. 14A-C is inserted into the skin at the donor site in such a way that the hair enters the punch's interior. As the hair and follicle enter the punch's interior, its curl is accommodated by the posterior notch. Because the posterior notch is sufficiently long in the proximal direction and its laterally-extending base lacks a sharpened cutting edge, the curled hair and follicle is less likely to be damaged by contact with the edges of the posterior notch during punch insertion. As the punch is further inserted from its positions in "C" and "D" to follow the follicle as the prong-like members' cutting edges cut the surrounding tissue, the curled shape of the follicle causes it to contact the posterior internal surface of the punch and, perhaps, the laterally-extending base 434 of the notch 414. As the punch is advanced past the follicle, it remains undamaged by the cutting edges of the punch by passing through the notch. Once the punch has penetrated sufficiently, it can be partially rotated back and forth if desired, resulting in an arcuate cut in the tissue substantially circumscribing the curled follicle, while the follicle itself is spared by its clearance within the notch and the lack of a cutting edge on the base member 434.

The placement of a "V"-shaped notch on the anterior side of the punch illustrated in FIGS. 12A-C is preferred because the cutting edges circumscribing that notch shape cut more efficiently and controllably, and contact with the follicle (which points away from the anterior is unlikely.

Those of ordinary skill in the art will recognize, however, that the anterior and posterior notches could be the same shape—e.g., either generally V-shaped, generally "U" shaped, generally "'V' plus 'U'-shaped, or other desired shape—and such combinations are within the scope of the invention.

Regardless of the specific version of follicle punch utilized, the inclusion of an ultrasonic transducer coupled to the punch and selectively operable to enhance the cutting operation is desirable. The transducer is mounted within a handpiece to which the punch is attached in a manner analogous to the transducer, handpiece and scaler tip of an ultrasonic dental scaler. The punch may be further mounted for reciprocating pivoting movement within the handpiece so as to move in such manner with or without ultrasonic vibratory movement. Likewise, the configuration may be such that ultrasonic vibratory movement can be generated with or without the pivoting movement.

In practice, it has been found that an adjustable degree of longitudinally reciprocating ultrasonic movement is desirable in that the appropriate degree of movement is a function of the subject's skin thickness and tissue, with higher settings being suitable when cutting through thicker skin or scar tissue for example. The use of the ultrasonic movement permits the surgeon or other operator of the equipment to better use his/her "fine motor" muscle movement to more precisely make the required incisions with greater sensitivity and finesse.

Although the present invention and its advantages have been described in detail, it should be understood that various changes, substitutions and alterations can be made herein without departing from the spirit and scope of the invention as will be defined by appended claims.

I claim:
1. A follicle punch comprising:
   a generally tubular body disposed about a generally longitudinal axis between distal and proximal ends, and having
      an inner surface and an outer surface;
      a distal cutting end region terminating distally in an opposing pair of distally-extending prong-like members, and
      an anterior notch and a posterior notch arranged between the pair of prong-like members at the distal end of the generally tubular body, wherein the posterior notch extends further proximately than the anterior notch;
   wherein each of the prong-like members further comprises a convex curved anterior cutting edge and a concave curved posterior cutting edge,
   wherein the curved anterior cutting edge and the curved posterior cutting edge meet at a cutting tip,
   wherein the prong-like members are aligned with each other such that they have essentially the same shape as each other and wherein the cutting tip of each prong-like member is oriented at an angle relative to the longitudinal axis of the generally tubular body towards the curved posterior cutting edge.

2. The punch of claim 1 wherein said one of the notches extends further than the other notch by a length in the range of 0.25 mm to 2 mm, inclusive.

3. The punch of claim 2 wherein said one of the notches has a generally "V"-shaped distal segment, and a generally "U"-shaped proximal segment extending proximally from the distal segment.

4. The punch of claim 3 wherein the U-shaped proximal segment includes two proximally extending legs connected by a generally laterally extending base at the proximal end of the notch, and wherein at least a portion of the legs carry respective cutting edges formed by respective beveled surfaces.

5. The punch of claim 4 wherein the base of the U-shaped notch lacks a cutting edge formed by a beveled cutting surface.

6. The punch of claim 5 wherein said other of the notches is generally V-shaped.

7. The punch of claim 6 wherein said other of the notches includes two proximally extending legs that carry respective cutting edges formed by respective beveled surfaces.

8. The punch of claim 5 wherein said other of the notches has a generally "V"-shaped distal segment, and a generally "U"-shaped proximal segment extending proximally from the distal segment.

9. The punch of claim 1 including
a handpiece coupled to the punch for enabling the punch to be controllably manipulated by a user in removal of a hair follicle from a targeted donor site, and
an ultrasonic transducer within the handpiece and coupled to the punch and selectively operable by the user to induce ultrasonic movement in the punch to enhance cutting to controllably cut skin and tissue around a targeted donor site.

10. The punch of claim 9 wherein the ultrasonic movement is generally axial.

11. The punch of claim 1 wherein at least one of the notches is generally V-shaped.

12. The punch of claim 1 wherein at least one of the notches is generally U-shaped.

13. The punch of claim 1 including
a handpiece coupled to the punch for enabling the punch to be controllably manipulated by a user in removal of a hair follicle from a targeted donor site, and
a vibrating tool within the handpiece and coupled to the punch and selectively operable by the user to induce ultrasonic movement in the punch to enhance cutting to controllably cut skin and tissue around a targeted donor site.

14. The punch of claim 1 wherein the prong-like members include beveled surfaces terminating at the cutting edges.

15. The punch of claim 14 wherein the beveled surfaces are formed on the inside surface of the tubular punch body.

16. The punch of claim 15 wherein the cutting edge formed by the beveled cutting surface is at the punch's outer diameter.

17. The punch of claim 14 wherein the cutting edge formed by the beveled cutting surface is at the punch's outer diameter.

* * * * *